United States Patent
Bambha et al.

(10) Patent No.: US 10,067,049 B1
(45) Date of Patent: Sep. 4, 2018

(54) METHOD AND SYSTEM FOR MULTI-PASS LASER-INDUCED INCANDESCENCE

(71) Applicant: National Technology & Engineering Solutions of Sandia, LLC, Albuquerque, NM (US)

(72) Inventors: Ray Bambha, Livermore, CA (US); Hope A. Michelsen, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 67 days.

(21) Appl. No.: 15/239,634

(22) Filed: Aug. 17, 2016

(51) Int. Cl.
G01N 15/00 (2006.01)
G01N 21/00 (2006.01)
G01N 15/14 (2006.01)
G01N 21/71 (2006.01)

(52) U.S. Cl.
CPC ....... *G01N 15/1434* (2013.01); *G01N 21/718* (2013.01)

(58) Field of Classification Search
None
See application file for complete search history.

(56) References Cited

U.S. PATENT DOCUMENTS 3,792,272 A * 2/1974 Harte ................. G01N 21/3504
250/338.1
4,953,976 A * 9/1990 Adler-Golden ........ G01N 21/65
356/301
5,528,040 A * 6/1996 Lehmann ................. G01J 3/42
250/343
5,818,578 A * 10/1998 Inman ................. C23C 16/4412
356/246
6,563,583 B2 * 5/2003 Ortyn ..................... C07K 1/047
356/399

(Continued)

FOREIGN PATENT DOCUMENTS

WO    2011064806 A2    6/2011

OTHER PUBLICATIONS

Perry, et al., "Controllable Pulse Compression in a Multiple-Pass-Cell Raman Laser", In Optics Letters, vol. 5, No. 7, Jul. 1980, pp. 288-290.

(Continued)

*Primary Examiner* — Shawn Decenzo
*Assistant Examiner* — Jarreas C Underwood
(74) *Attorney, Agent, or Firm* — Medley, Behrens & Lewis, LLC

(57) ABSTRACT

Various technologies for measurement of properties of a particulate suspended in a gas phase via laser-induced incandescence (LII) are described herein. A beam of light can be emitted into a multi-pass optical cell using a laser. The multi-pass optical cell comprises a system of one or more mirrors that repeatedly reflects the beam through a measurement region, stimulating incandescence of particulates present in the measurement region. An LII detection system having a field of view that encompasses the measurement region then receives blackbody or quasi-blackbody radiation emitted by the incandescing particles and outputs data indicative of one or more properties of the particulates in the measurement region.

20 Claims, 7 Drawing Sheets

(56) References Cited

U.S. PATENT DOCUMENTS

| | | | | |
|---|---|---|---|---|
| 6,809,820 B2* | 10/2004 | Snelling | ............... | G01N 21/71 |
| | | | | 356/315 |
| 7,084,963 B2* | 8/2006 | Leipertz | ............... | F01N 1/00 |
| | | | | 250/339.13 |
| 7,307,716 B2* | 12/2007 | Silver | ............... | G01N 21/031 |
| | | | | 356/246 |
| 7,477,377 B2* | 1/2009 | Silver | ............... | G01N 21/031 |
| | | | | 356/246 |
| 7,876,443 B2* | 1/2011 | Bernacki | ............ | G01N 21/031 |
| | | | | 356/432 |
| 2004/0238745 A1* | 12/2004 | Pedersen | ............ | G01N 21/3151 |
| | | | | 250/343 |
| 2016/0202175 A1* | 7/2016 | Sawyers | ............ | G01N 21/031 |
| | | | | 356/402 |

OTHER PUBLICATIONS

Trutna, et al., "Multiple-Pass Raman Gain Cell", In Applied Optics, vol. 19, No. 2, Jan. 15, 1980, pp. 301-312.

Tuzson, et al., "Compact Multipass Optical Cell for Laser Spectroscopy", In Optics Letters, vol. 38, No. 3, Feb. 1, 2013, pp. 257-259.

\* cited by examiner

METHOD AND SYSTEM FOR MULTI-PASS LASER-INDUCED INCANDESCENCE

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Laser-induced incandescence (LII) is an analytical technique that can be used for in-situ measurements of soot or other particles in environments such as flames, combustion chambers, the atmosphere, etc. Unlike most laser-based gas-phase diagnostic techniques, LII is a technique that is not performed along the line-of-sight of the laser and is not typically strongly dependent on laser wavelength. Rather, LII is directed toward heating particulates suspended in a gas phase to incandescence, thereby stimulating emission of blackbody or quasi-blackbody radiation. Because the thermal radiation is incoherent and emits with little or no preference for direction, its measurement is typically performed off-axis with respect to the laser propagation, and the amount of incandescent radiation received by an LII detector will increase proportionally as the solid angle of the region observed by the detector is increased.

The blackbody or quasi-blackbody spectrum of the incandescent radiation will vary depending on the temperature that the particles reach and their composition, and the total emission will be strongly dependent on the temperature that the particles reach. Measurements of the spectrum of the incandescence allow the temperature of the particles to be estimated. As particles are heated to their vaporization temperature, a maximum temperature will be reached that is dependent on the material properties of the particles. Levels of emission of incandescent radiation by the particles over time as the particles heat depends on material and optical properties of the particles. The amount of LII scales with the volume of material in the particles. The heating rate of particles during LII is proportional to the absorption of the particles at the excitation wavelength, and the absorption spectrum of the particles is influenced by the material composition and optical properties. Properties of an analyte specimen such as spatial distribution, concentration, absorption coefficient, and composition can be determined based upon analysis of the radiation emitted as a result of the incandescence of the analyte.

LII relies on the extremely high spatial coherence of laser radiation to generate the high optical intensities required to heat particles to incandescence. A key parameter of the laser is its fluence, a measure of energy delivered per unit area. Unlike most laser-based gas-phased diagnostic techniques, LII has a non-linear dependence on the laser energy. For a given particulate analyte specimen, a certain threshold fluence of the laser must be reached for the laser to impart enough energy to the particulates to bring them to their vaporization point and produce incandescence at the particle vaporization temperature.

Information that can be gleaned from LII measurements of a specimen can depend in part on a level of incandescence signal that can be stimulated in the specimen by the laser. In general, this signal level is higher when 1) a density of the particulate analyte is higher or 2) when a larger area is illuminated by the laser while maintaining a same level of fluence. The density of the particulate analyte is sample-dependent, and is generally a value desirably measured rather than a parameter to be controlled. Thus, when the density of the analyte is relatively low, a diameter of the laser beam used to illuminate the sample can be increased to cause a greater level of signal incandescence. In order to maintain a required threshold fluence for a larger beam diameter at a given pulse repetition rate, however, the power output of the laser must be increased. In some cases, increasing the power output of the laser is prohibitive, as the power output required to generate a desired signal level is too high to practically realize. In other cases, a sufficiently high-power laser may be built, but it may be so large or unwieldy as to be unsuitable for in-situ field measurements of samples.

SUMMARY

The following is a brief summary of subject matter that is described in greater detail herein. This summary is not intended to be limiting as to the scope of the claims.

Various technologies for improving LII measurement of particulate samples are disclosed herein. In an exemplary embodiment, a laser emits a beam of light into a multi-pass optical cell that is configured to reflect the beam through a measurement region a plurality of times. In the example, the laser is configured so that the beam causes incandescence of particulate matter upon each pass through the measurement region. Thus, on each subsequent pass of the laser through the measurement region, the laser illuminates a greater area of the measurement region. Since the laser is not strongly attenuated as it interacts with the particulate analyte in the measurement region (e.g., the beam energy is attenuated by less than 5% per pass through the measurement region), the beam retains approximately a same fluence on subsequent passes through the measurement region as for the first pass. Therefore, by repeatedly reflecting the laser back through the measurement region, the multi-pass optical cell effectively increases an area of illumination of the laser without requiring an increase in the laser's power.

In an additional embodiment, the LII emission is measured in multiple wavelength bands during the multiple passes of the laser through the sample region to obtain information on the temperatures that the particles reach through laser heating.

In still another additional embodiment, a change in radiation emitted by the particles over a window of time is measured as the particles are heated by the laser, and the temporal LII measurement is repeated at multiple excitation wavelengths. These temporal measurements may be made using only a single pass of the excitation laser(s) through the measurement volume, or the measurements may be made using a multi-pass optical cell.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
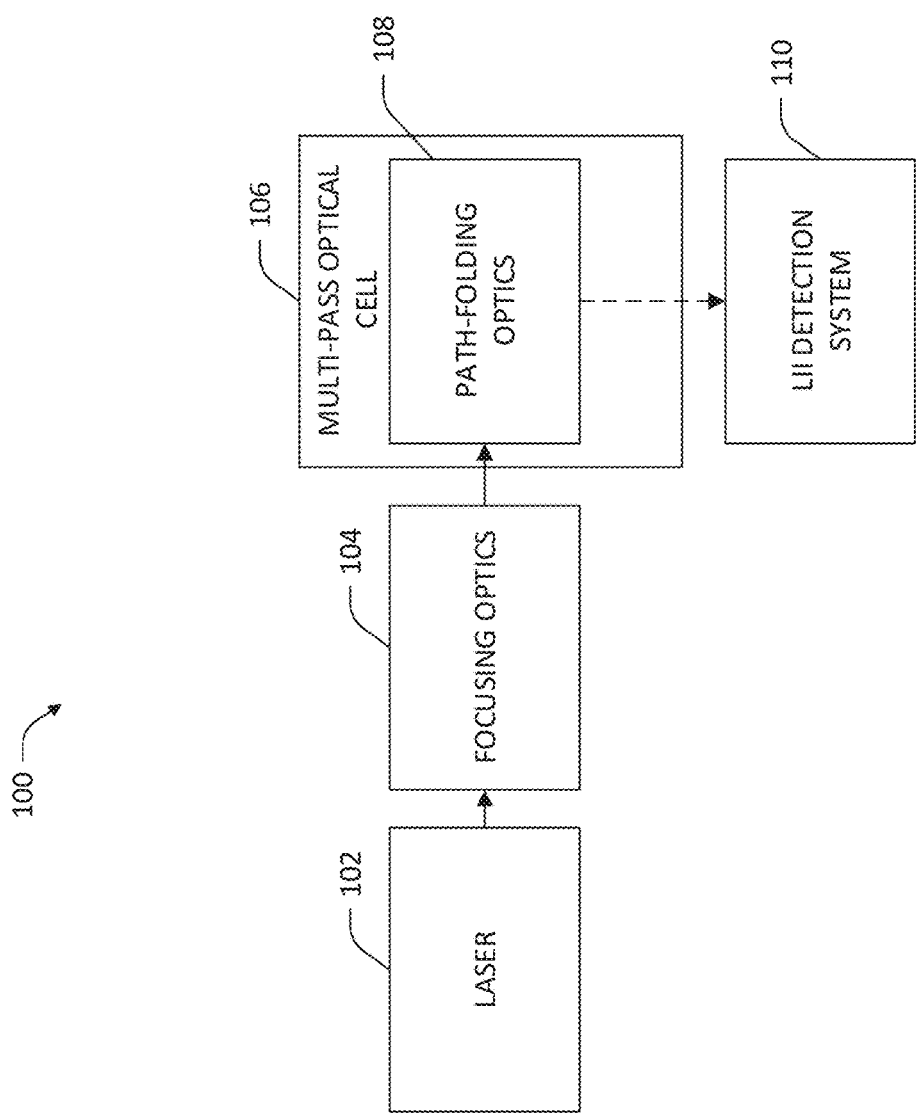
FIG. 1 is a functional block diagram of an exemplary system that facilitates multi-pass LII.

Various technologies pertaining to multi-pass laser-induced incandescence (LII) are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended in some instances to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Additionally, as used herein, the term "exemplary" is intended to mean serving as an illustration or example of something, and is not intended to indicate a preference.

With reference to FIG. 1, an exemplary system 100 that facilitates multi-pass LII is illustrated. The system 100 includes a laser 102 that emits a beam of light to a system of focusing optics 104, which focuses and directs the beam of light to a multi-pass optical cell 106. The multi-pass optical cell 106 comprises a system of path-folding optics 108 that repeatedly directs the beam of light through a measurement region, or cavity, in which resides a sample to be measured via LII. Thus, the multi-pass optical cell 106 causes the beam to make multiple "passes" through the measurement region. As used herein, the term measurement region is intended to refer to any area or volume into which a laser beam can be emitted to stimulate incandescent emission from a particulate analyte. The particulate analyte can be any particulate that can absorb laser light and be heated to temperatures sufficiently high that the particles emit thermal radiation via incandescence. For example, the particulate analyte can comprise soot particles. In another example, the particulate analyte can comprise metal particles such as engineered nano-materials used in catalytic processes. In still another example, the particulate analyte can comprise a mineral such as hematite. The beam of light passes through the measurement region a plurality of times according to a path determined by the structure of the path-folding optics 108, as described in greater detail below with respect to certain exemplary configurations illustrated in FIGS. 2-5. As the beam passes repeatedly through the measurement region, the beam excites particles of the analyte specimen present in the measurement region, bringing them to incandescence. The excited analyte particles emit blackbody or quasi-blackbody radiation that is received by an LII detection system 110. The LII detection system 110, responsive to receiving the emitted radiation from the analyte particles in the measurement region, then outputs data indicative of one or more properties of the analyte within the measurement region. These properties can include spatial distribution of the particles, density of the particles, etc.

The multi-pass LII system 100 allows an area illuminated by a laser to be increased for a substantially same fluence as compared with conventional LII measurement techniques. As the beam passes through the measurement region, attenuation is small, e.g., between 0.01%-5%. Thus, the beam retains most of its energy each time it passes through the measurement region. When the beam from the laser 102 passes into the multi-pass optical cell 106 to the path-folding optics 108, the optics 108 direct the beam back into the measurement region a number of times. Each time the beam passes back through the measurement region, the beam illuminates an additional portion of the measurement region, exciting additional analyte particles and bringing them to incandescence. Since the beam is not strongly attenuated when it passes through the measurement region, the beam can retain sufficiently high fluence on subsequent passes to bring more particles to incandescence. Thus, the path-folding optics 108 redirect the laser beam to effectively increase the area of illumination by the beam while retaining a beam fluence necessary to cause incandescence of the particulate analyte. This allows incandescence signal levels to be increased without requiring a higher-energy laser to be used, thereby improving performance of the LII detection system 110.

Unlike laser-absorption spectroscopy techniques, which are directed toward detection of absorption of particular wavelengths along the line of sight of the light emitted by a laser, the LII technologies described herein are directed toward increasing incandescence, which radiates isotropically, in a particulate sample without requiring a laser to have a higher power output. Thus, for example, the systems and methods described herein allow a laser beam to maintain sufficient fluence upon subsequent passes through a measurement region that the beam still reliably causes incandescence of a particulate sample. In another example, the technologies described herein aid in uniform illumination of the measurement region, which allows properties of a particulate sample in the measurement region to be more easily inferred from the intensity of incandescence observed in the region. These advantages of the techniques set forth herein to LII measurements are not applicable to line-of-sight optical techniques.

The mirrors used in the path-folding optics 108 are high-reflectivity mirrors. In an example, the mirrors of the path-folding optics 108 reflect 80% or more of the energy of an incident beam of light. In another example, the mirrors of the path-folding optics 108 reflect 95% or more of the energy of an incident beam of light. In still another example, the mirrors of the path-folding optics 108 reflect 99% or more of the energy of an incident beam of light. The high reflectivity mirrors of the path-folding optics allows the beam of light to retain enough energy upon each pass to reliably cause incandescence of the analyte sample.

Exemplary embodiments of the multi-pass optical cell 106 for use in LII measurements are discussed below with respect to FIGS. 2-5. Certain exemplary aspects of the multi-pass optical cell 106 are described below with reference to particular configurations of a multi-pass optical cell, but it is to be understood that certain of these aspects are applicable to the multi-pass optical cell 106 or the path-folding optics 108 generally, and can be implemented with respect to some or all of the exemplary multi-pass cells described below with respect to FIGS. 2-5.

Figure 2:
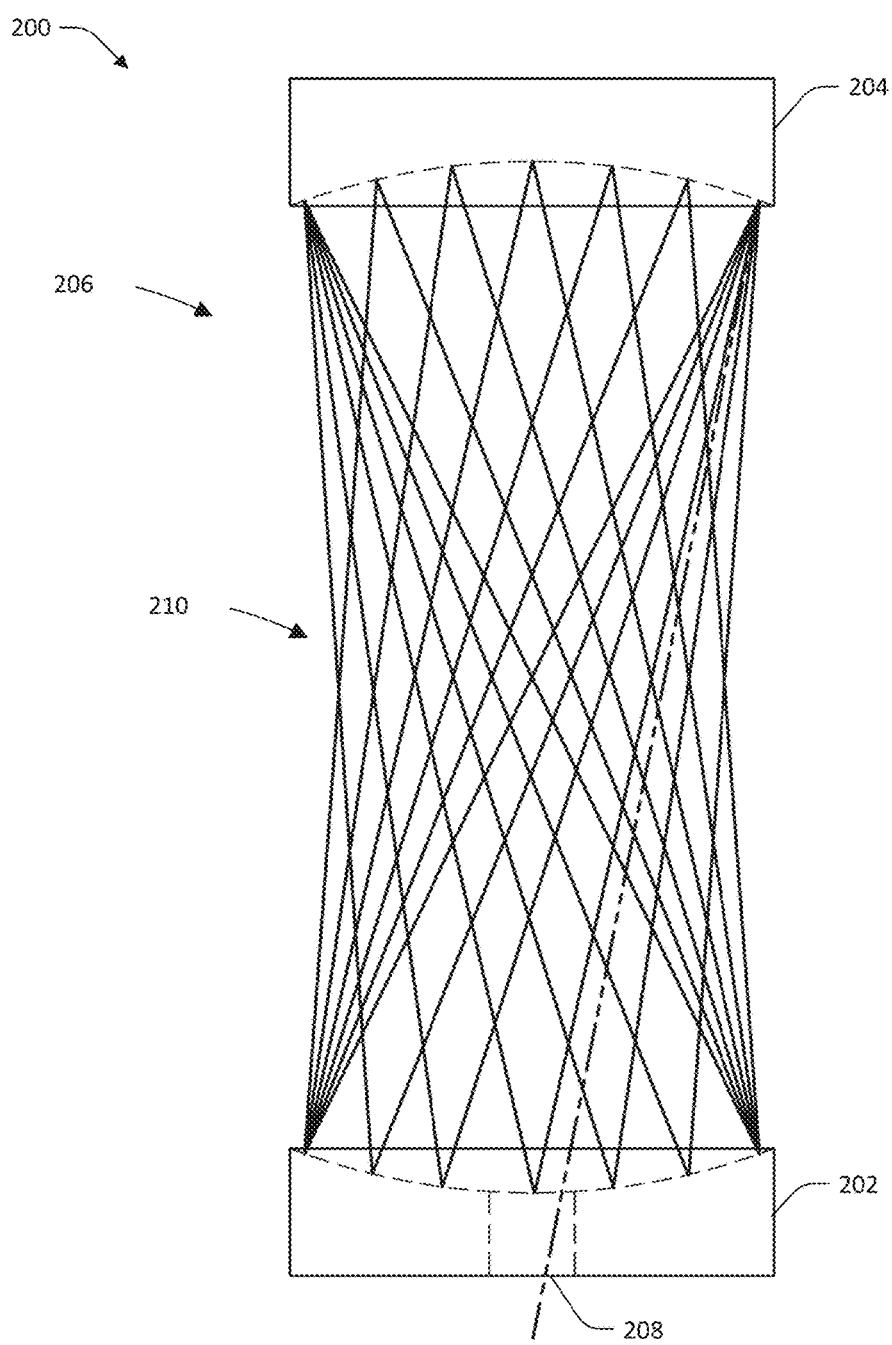
FIG. 2 illustrates an exemplary Herriott cell that facilitates multi-pass LII.

Referring now to FIG. 2, an exemplary multi-pass Herriott cell 200 that facilitates multi-pass LII is illustrated. The Herriott cell 200 comprises two concave mirrors 202-204 that face one another and reflect a laser beam repeatedly through a measurement region 206 between the two mirrors 202-204. The measurement region 206 contains the analyte specimen (not illustrated) to be measured via LII. The laser beam enters the Herriot cell 200 by an aperture 208 at the center of the first mirror 202. The laser beam is then reflected by the second mirror 204 back through the measurement region 206, after which it is reflected by the first mirror 202 into the measurement region 206 once more. A number of passes of the beam through the cell 200 can be controlled by modifying a distance between the first and second mirrors 202-204. As the beam bounces between the mirrors 202-204, passing through the measurement region 206 containing the analyte specimen each time, the beam strikes the mirrors 202-204 forming a circular pattern around the center of each mirror. The ultimate path of the beam can be seen to define an approximately hourglass-shaped volume, with a narrower region at or near a midpoint 210 between the two mirrors 202-204.

In an exemplary embodiment, the beam emitted by the laser 102 has a Gaussian intensity profile in the direction of propagation. The mirrors 202-204 can be configured to refocus the beam each time it is reflected, so that the beam has a substantially same diameter each time the beam passes through a plane at the middle 210 of the measurement region 206. When the beam has a substantially same diameter each time it passes through the plane at the center 210 of the measurement region 206, a total energy delivered to the analyte sample can more reliably be determined. Knowing the approximate total energy delivered to the analyte, properties of the analyte sample such as spatial distribution, density, particle type, etc. can be inferred from levels of incandescence, spectral emission, and temporal change of levels of emitted radiation detected by the LII detection system 110. In exemplary embodiments of the multi-pass cell 106, the arrangement and configuration of mirrors is adapted to colocation of beam waists of the beam within a localized area in the measurement region 206 that is within a field of view of the LII detection system 110. For example, mirrors of the path-folding optics 108 can be configured so that the radius of curvature of the beam as it impinges on the mirrors is matched to the radius of curvature of the mirrors. In another example, the focusing optics 104 and the path-folding optics 108 can focus the beam so that upon reaching the analyte sample in the measurement region 206, the beam has a greatest possible beam diameter at a beam fluence that still reliably brings the analyte sample to incandescence.

Figure 3:
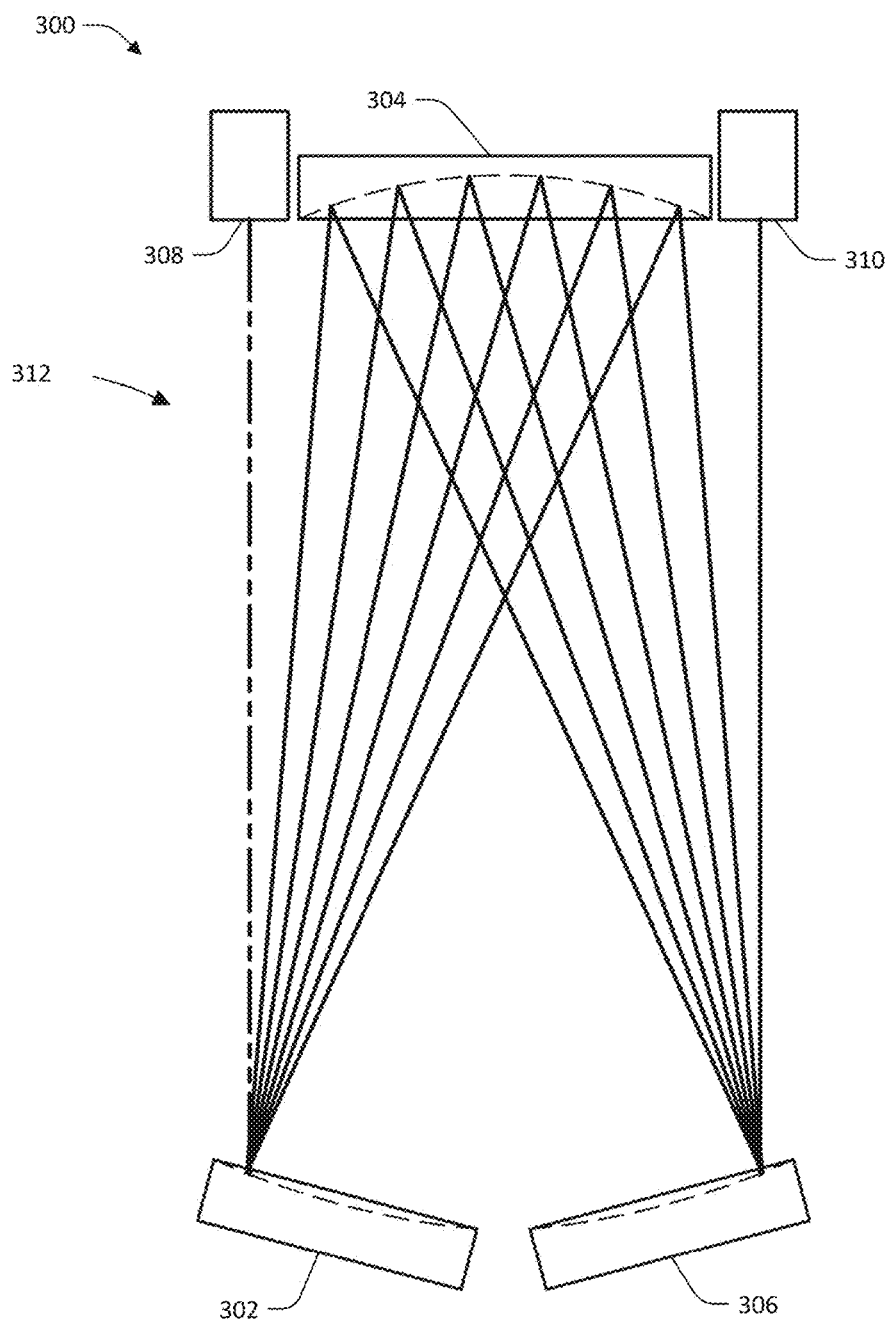
FIG. 3 illustrates an exemplary White cell that facilitates multi-pass LII.

Referring now to FIG. 3, another exemplary multi-pass optical cell 300 that facilitates multi-pass LII is illustrated. The multi-pass optical cell 300 is a White cell, comprising a first mirror 302 that receives a beam of light from a laser, a second mirror 304 that receives the beam upon reflection from the first mirror 302, and a third mirror 306 that receives the beam reflected from the second mirror 304. The third mirror 306 then reflects the beam back to the second mirror 306, whereupon it is again reflected to the first mirror 302. The first and third mirrors 302 and 306 are arranged facing the second mirror 304. A number of passes of the beam through the cell 300, bouncing from the first mirror 302 to the second 304 to the third 306 and back again depends on a rotational alignment of the mirrors 302-306. The beam of light passes into the cell 300 through a first aperture 308 that is positioned to direct the beam to the first mirror 302. After making the number of passes through the cell 300, the beam of light is reflected out of the cell 300 through a second aperture 310 by the third mirror 306. In other embodiments, the beam of light can exit the cell 300 via the first aperture 308 after reflection from the first mirror 302.

In contrast to the multi-pass Herriott cell 200, wherein the beam path through the cell 200 defines an hourglass-shaped volume, the beam travels through the White cell 300 along a path that lies in a substantially same plane. A spatial distribution of the beam path can affect a spatial resolution of LII data. For example, stimulation of incandescent emission from the particulate analyte along a linear or planar beam path (e.g., as shown in FIG. 3 with respect to the White cell 300) can be suitable for mapping a spatial distribution of the particulate analyte. In another example, a three-dimensional beam path defining a volume of revolution (e.g., as shown in FIG. 2 with respect to the Herriott cell 200) can be suitable for detecting an average concentration of the particulate within the measurement region.

While the mirrors 302-306 are shown in FIG. 3 as being curved, concave mirrors, it is to be understood that the mirrors 302-306 can be flat, planar mirrors. In an exemplary embodiment, the mirrors 302-306 of the cell 300 can be flat when the beam of light has sufficiently high diameter that divergence of the beam will not cause the fluence of the beam to be reduced below a threshold level necessary to cause incandescence of the analyte.

Figure 4:
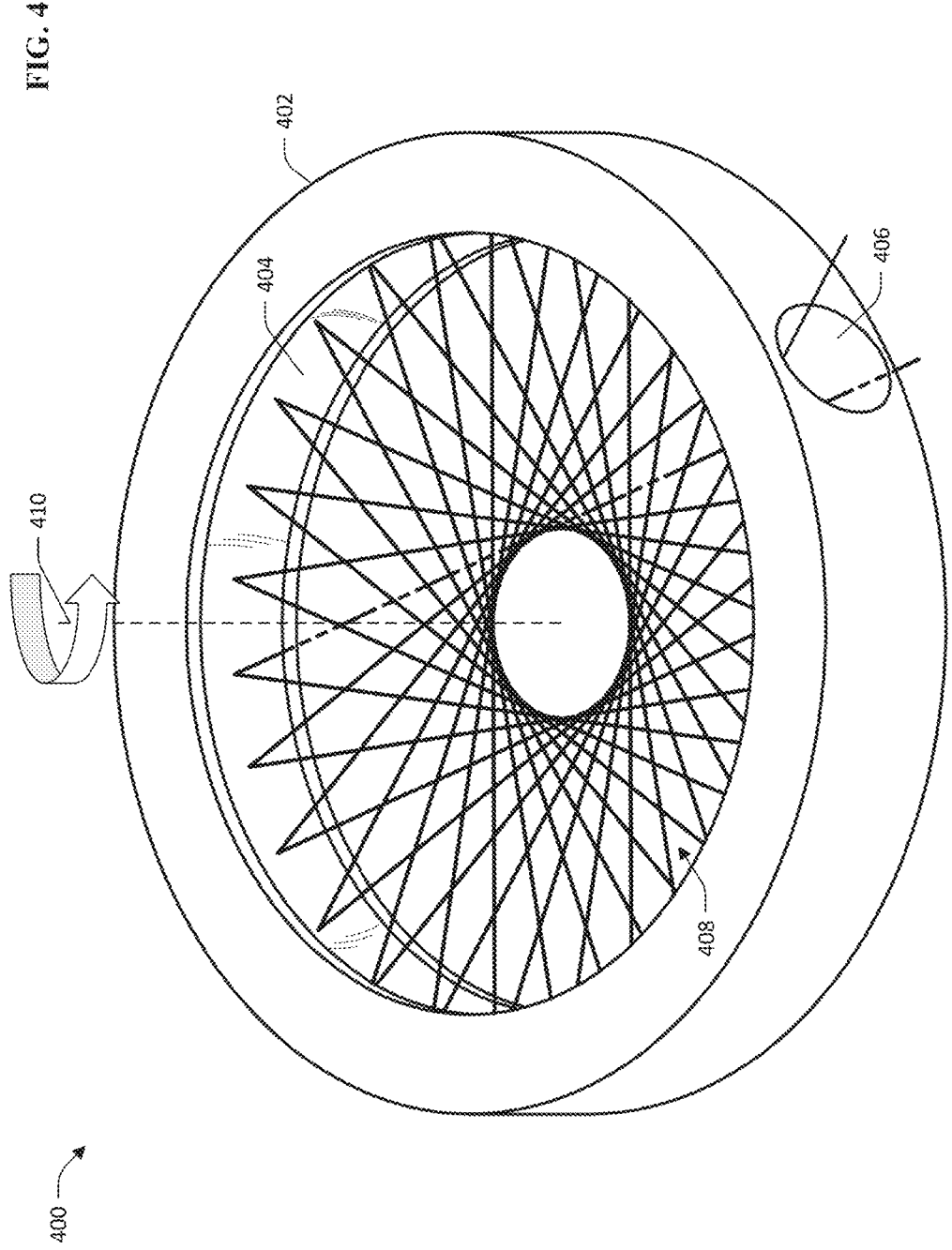
FIG. 4 illustrates an exemplary circular cell that facilitates multi-pass LII.

Referring now to FIG. 4 an exemplary circular multi-pass LII cell 400 is illustrated. The circular cell 400 comprises an outer ring portion 402 that surrounds and contains a circular mirror 404. The cell 400 further comprises an aperture 406 through which a laser beam is passed. The beam is reflected a plurality of times by the mirror 404, and each time the beam is reflected it passes through a measurement region 408 in the interior of the cell 400, causing incandescence of a particulate analyte. The configuration of the cell 400 is well-suited to LII measurement in flames, exhaust streams, or combustion chambers having cylindrical symmetry. In some embodiments, the cell 400 can be rotated about an axis 410 passing through the center of the measurement region 408. As the cell 400 is rotated, the path of the laser beam through the cell 400 sweeps out a substantially disc-like area. Thus, the circular multi-path LII cell can be used to measure properties of a particulate analyte in a disc-shaped region. The cell 400 can further be translated along the axis in addition to being rotated around the axis. If the cell 400 is both rotated and translated in this way, the cell 400 can be used to measure properties of the particulate analyte in a cylindrical volume over time. In still other embodiments, an angle of incidence of the beam entering the cell 400 can be dithered in a predetermined manner to sweep the beam pattern in an azimuthal direction, thereby providing uniform illumination over a portion of the disc-shaped region. In these embodiments, a rotating mirror, prism, or acousto-optic scanner (not pictured) can be used to steer the beam for dithering.

Figure 5:
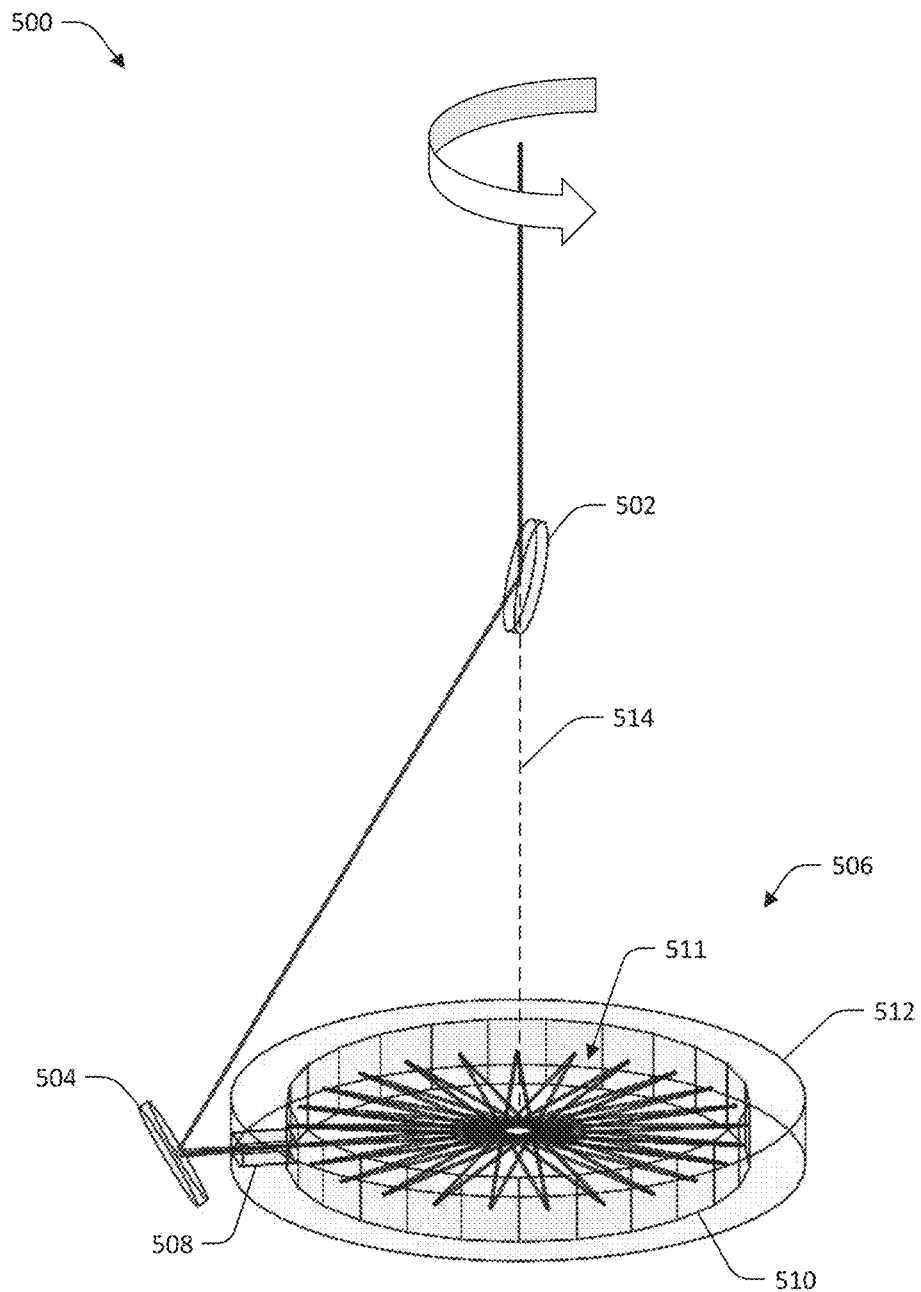
FIG. 5 illustrates an exemplary polygonal cell that facilitates multi-pass LII.

Referring now to FIG. 5, an exemplary multi-pass optical system 500 for making LII measurements is illustrated. The system 500 comprises a first fold mirror 502 that receives a laser beam from a stationary laser (not pictured) and reflects the beam to a second fold mirror 504. The second fold mirror 504 is positioned to reflect the beam into a polygonal multi-pass optical cell 506 through an aperture 508. The multi-pass optical cell 506 comprises a plurality of mirrors (e.g., mirror 510) that are connected to form edges of a polygonal shape. The aperture 508 is located at one of the edges of the polygonal shape, and so the laser beam enters the cell 506 and travels along a path that lies in a same plane as the polygonal shape. As the beam travels along the path, it is reflected by each of the mirrors in the plurality of mirrors at least once. It is to be understood that the multi-pass optical cell 506 can, in different configurations, have different numbers of mirrors, and thusly that the interior of the cell 506 can have different polygonal shapes. The mirrors that form the interior of the cell 506 reflect the beam repeatedly through a measurement region 511 in the interior of the polygonal shape of the cell 506. The mirrors forming the polygonal interior of the cell 506 can be contained within an outer structural ring 512.

As shown in FIG. 5, the multi-pass optical system 500 can be rotated around an axis 514 that passes through the center of the cell 506 and is collinear with an original path of the laser beam before it reaches the first fold mirror 502. The configuration of the multi-pass optical system 500 allows the cell 506 to be rotated in order to measure incandescence of a particulate analyte in a disc within the measurement region 511 while allowing the laser that stimulates incandescence of the particulate to be stationary. This arrangement can simplify construction of certain field-deployable LII systems by eliminating the need for a movable power source for the laser. Similar to the circular cell 400, the system 500 can be translated along the axis of rotation 514 in order to facilitate measurement of particulate properties in a cylindrical volume via LII.

Figure 6:
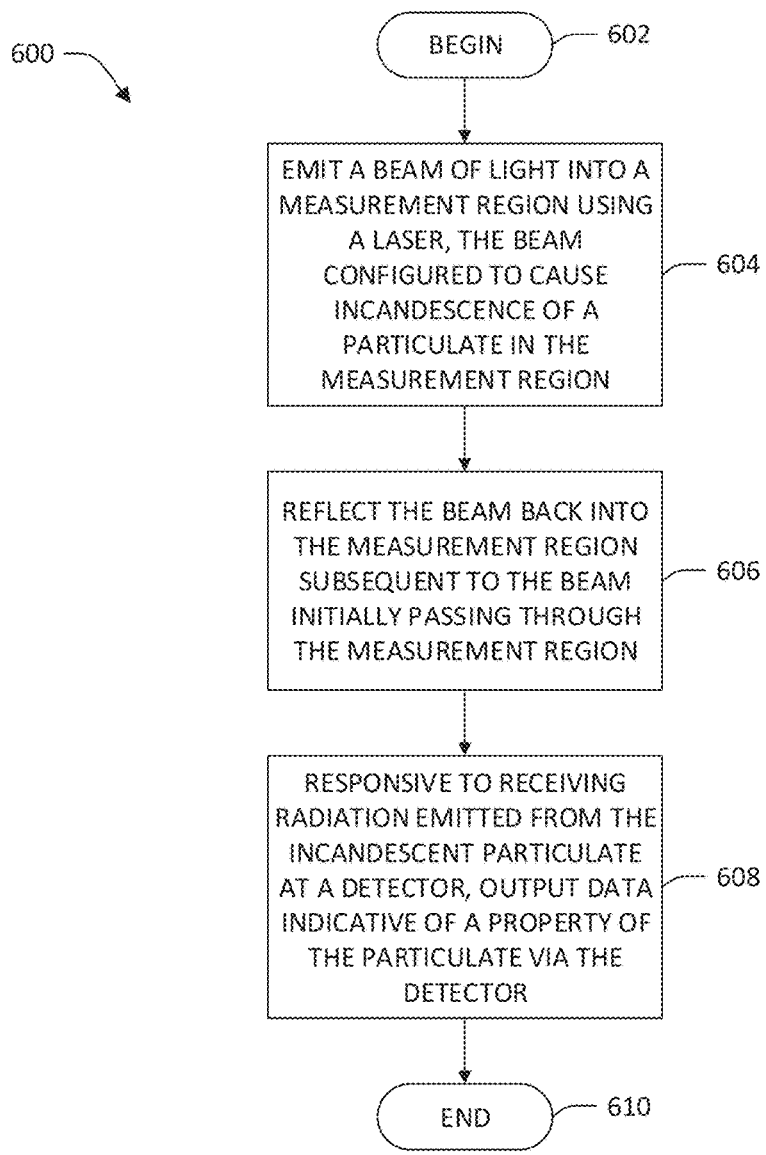
FIG. 6 is flow diagram that illustrates an exemplary methodology for analyzing properties of a particulate in a sample via multi-pass LII.

FIG. 6 illustrates an exemplary methodology relating to LII with multi-pass optical cells. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Referring now to FIG. 6, a methodology 600 that facilitates measurement of particulate properties via LII using multi-pass optical cells is illustrated. The methodology 600 begins at 602, and at 604 a beam of light is emitted into a measurement region by a laser. The beam emitted by the laser is configured to cause incandescence of a particulate analyte within the measurement region. For example, the laser can be configured to have a beam fluence that is above a threshold fluence necessary to bring the particulate to incandescence. At 606, the beam is reflected back into the measurement region subsequent to the beam initially passing through the measurement region. In an example, the beam can be reflected back into the measurement region by a mirror that is part of a larger system of path-folding optics within a multi-pass optical cell. In the example, the mirror can have properties that are dependent on the structure of other optical elements in the system of path-folding optics. By way of example, the mirror can be a concave mirror that is configured to refocus the beam so that beam waists of the beam are located within a localized region in view of an LII detector. At 608, an LII detector outputs data indicative of a property of the particulate responsive to receiving radiation emitted from incandescence of the particulate analyte in the measurement region, whereupon the methodology 600 ends at 610.

Other aspects pertinent to techniques, systems, and technologies discussed herein are now described. In an embodiment, optical and compositional properties of a particulate analyte can be determined by comparing changes of LII of the particulate over time for multiple laser excitation wavelengths. Thus, each of one or more lasers can be configured to emit pulses having respective excitation wavelengths into a measurement region comprising the particulate analyte. For each pulse emitted into the measurement region, an LII detector having a line of sight into the measurement region can receive incandescent radiation emitted by the particulate over a window of time and output data indicative of one or more properties of the particulate over the window of time based upon the received radiation. Thus, for each of a plurality of pulses of different wavelengths, a respective temporal profile of LII emission can be output by the LII detector. By comparing these profiles, various optical and compositional properties of the particulate can be determined.

Figure 7:
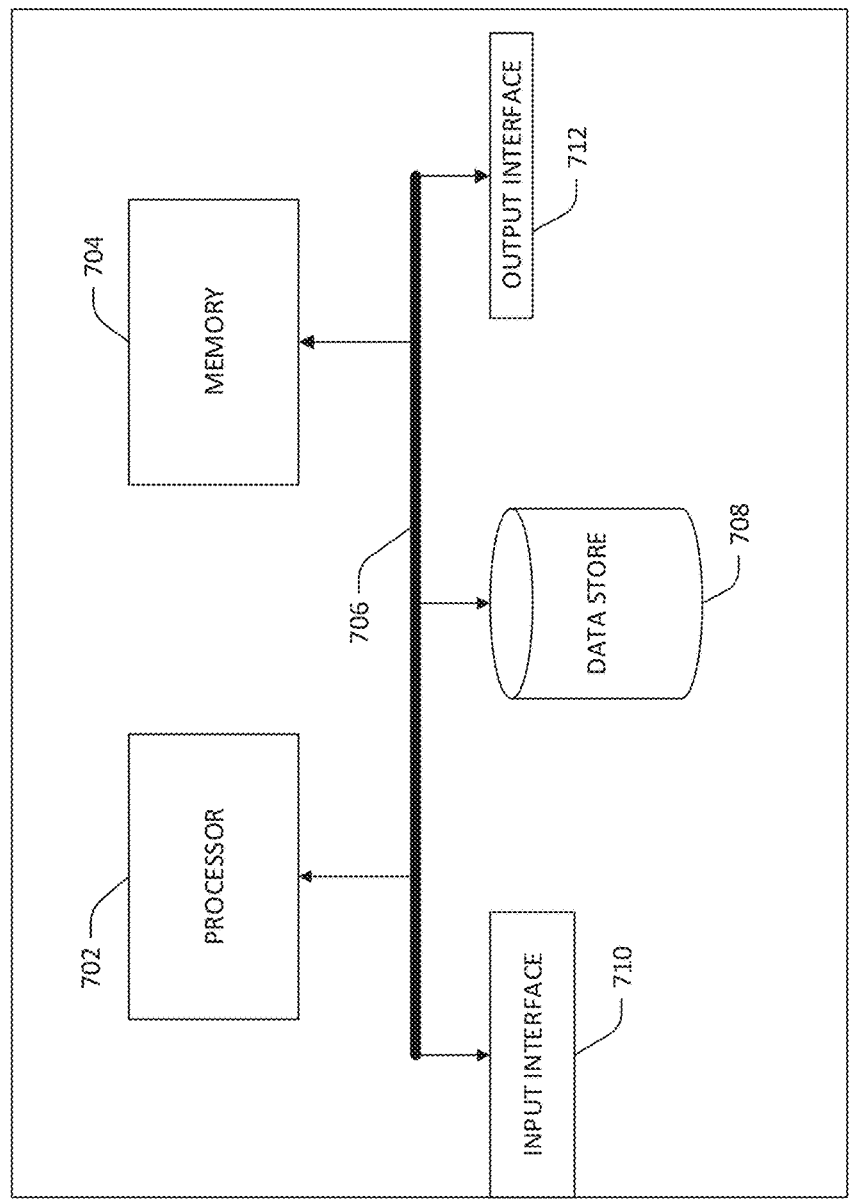
FIG. 7 is an exemplary computing system.

Referring now to FIG. 7, a high-level illustration of an exemplary computing device 700 that can be used to facilitate with the systems and methodologies disclosed herein is illustrated. For instance, the computing device 700 may be used in a system that interfaces with the LII detection system 110. By way of another example, the computing device 700 can be used in a system that controls operation of the laser 102. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store data output by the LII detection system 110.

The computing device 700 additionally includes a data store 708 that is accessible by the processor 702 by way of the system bus 706. The data store 708 may include executable instructions, LII detector data, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system for laser-induced incandescence (LII) measurement, comprising:
   a laser configured to cause incandescence of a particulate;
   a multi-pass optical cell, the cell comprising:
      a first mirror configured to receive a beam of light emitted from the laser and reflect the beam into a measurement region, the measurement region comprising the particulate, whereupon the beam causes incandescence of the particulate as the beam passes through the measurement region; and
      a second mirror configured to receive the reflected beam of light from the first mirror and reflect the beam back into the measurement region, whereupon the beam causes further incandescence of the particulate as the beam passes back into the measurement region; and
   a detection system configured to output data indicative of a property of the particulate in the measurement region based upon the incandescence of the particulate in the measurement region.

2. The system of claim 1, further comprising focusing optics, wherein the focusing optics receive the beam from the laser and focus the beam so that the beam is in focus within the measurement region.

3. The system of claim 2, wherein the first mirror and the second mirror are configured to refocus the beam so that the beam returns to focus as it passes through the measurement region.

4. The system of claim 2, the focusing optics further configured to cause beam waists of the beam to be within a field of view of the detection system.

5. The system of claim 1, wherein the beam is reflected by each of the first mirror and the second mirror into the measurement region a respective plurality of times.

6. The system of claim 1, wherein the multi-pass optical cell comprises a White cell, the White cell further comprising a third mirror, the third mirror positioned so that the third mirror receives the beam from the second mirror and reflects the beam back through the measurement region to the first mirror.

7. The system of claim 1, wherein the multi-pass optical cell comprises a Herriott cell, the first mirror and the second mirror each having a respective concave surface that receives the beam, the respective concave surfaces of the first and second mirrors facing one another, the first and second mirrors arranged so that a plurality of beam waists of the beam are within the measurement region in view of the detection system.

8. The system of claim 1, wherein the first and second mirrors are configured so that the beam propagates along a path that lies in a single plane.

9. The system of claim 1, wherein the first and second mirrors are highly reflective mirrors that attenuate energy of the beam by 5% or less upon each reflection.

10. The system of claim 1, the multi-pass cell comprising a plurality of mirrors, the plurality of mirrors comprising the first mirror and the second mirror, the plurality of mirrors arranged to form a polygon, wherein each of the mirrors in the plurality of mirrors is positioned at an edge of the polygon, and wherein the beam is incident upon and reflected from each of the mirrors in the plurality of mirrors at least once.

11. The system of claim 10, wherein the mirrors in the plurality of mirrors are flat mirrors.

12. The system of claim 10, the mirrors in the plurality of mirrors arranged so that the beam propagates along a path lying in a single plane.

13. The system of claim 10, further comprising:
a third mirror positioned between the laser and the multi-pass cell, the third mirror not belonging to the plurality of mirrors, the third mirror positioned to receive the beam from the laser; and
a fourth mirror, the fourth mirror not belonging to the plurality of mirrors and positioned to receive the beam reflected from the third mirror, whereupon the beam is reflected by the fourth mirror into the multi-pass cell.

14. The system of claim 13, wherein the third mirror, the fourth mirror, and the multi-pass cell are rotatable around an axis passing through a center of the polygon formed by the plurality of mirrors, the laser located at a fixed position, wherein the laser emits the beam along the axis.

15. The system of claim 10, wherein the multi-pass cell is translatable along an axis passing through a center of the polygon formed by the plurality of mirrors.

16. The system of claim 1, wherein the beam has a Gaussian intensity distribution in a direction of propagation of the beam.

17. A method, comprising:
emitting a beam of light into a measurement region using a laser, the measurement region containing particulate matter, the beam configured to cause incandescence of the particulate;
reflecting the beam back into the measurement region subsequent to the beam passing through the measurement region, wherein the beam causes additional incandescence of the particulate upon being reflected back into the measurement region; and
responsive to receiving radiation emitted from the incandescent particulate at a detector, outputting, via the detector, data indicative of a property of the particulate.

18. The method of claim 17, wherein the beam of light comprises light having a first wavelength, the method further comprising:
emitting a second beam of light into the measurement region, the second beam of light having a second wavelength, the second beam of light configured to cause incandescence of the particulate; and
responsive to receiving second radiation emitted from the incandescent particulate at a detector, the second radiation emitted responsive to the second beam of light causing incandescence of the particulate, outputting, via the detector, data indicative of one or more properties of the particulate.

19. A system for laser-induced incandescence (LII) measurement, comprising:
a laser that emits a beam of light into a measurement region, wherein a particulate to be measured is present in the measurement region, the beam configured to cause the particulate to emit incandescent radiation;
a first mirror configured to reflect the beam of light back into the measurement region subsequent to the beam passing through the measurement region, whereupon the beam causes the particulate to emit additional incandescent radiation when the beam passes back through the measurement region; and
a detector having a field of view encompassing at least a portion of the measurement region, the detector configured to output data indicative of a property of the particulate responsive to receiving the radiation emitted from the particulate.

20. The system of claim 19, wherein the first mirror is a circular mirror, the first mirror configured to reflect the beam of light back into the measurement region a plurality of times, the measurement comprising a region contained in the interior of the circular mirror.

* * * * *